(12) United States Patent
Pecherer (10) Patent No.: US 10,786,145 B2
(45) Date of Patent: Sep. 29, 2020

(54) LARYNGOSCOPE

(71) Applicant: Evgeny Pecherer, Netanya (IL)

(72) Inventor: Evgeny Pecherer, Netanya (IL)

( * ) Notice: Subject to any disclaimer, the term of this patent is extended or adjusted under 35 U.S.C. 154(b) by 226 days.

(21) Appl. No.: 15/312,652

(22) PCT Filed: May 21, 2015

(86) PCT No.: PCT/IB2015/053747
§ 371 (c)(1),
(2) Date: Nov. 20, 2016

(87) PCT Pub. No.: WO2015/177753
PCT Pub. Date: Nov. 26, 2015

(65) Prior Publication Data
US 2017/0202447 A1   Jul. 20, 2017

Related U.S. Application Data

(60) Provisional application No. 62/001,649, filed on May 22, 2014.

(51) Int. Cl.
*A61B 1/267*  (2006.01)
*A61B 1/00*  (2006.01)
*A61B 1/06*  (2006.01)

(52) U.S. Cl.
CPC .......... *A61B 1/267* (2013.01); *A61B 1/00025* (2013.01); *A61B 1/00036* (2013.01);
(Continued)

(58) Field of Classification Search
CPC ....... A61B 1/267; A61B 1/2673; A61B 1/008; A61B 1/06; A61B 1/0676; A61B 1/0684;
(Continued)

(56) References Cited

U.S. PATENT DOCUMENTS

| 3,985,131 A | 10/1976 | Buck et al. |
|---|---|---|
| 4,037,588 A | 7/1977 | Heckele |

(Continued)

FOREIGN PATENT DOCUMENTS

| GB | 2477084 A | 7/2011 |
|---|---|---|
| GB | 2491189 A | 11/2011 |

(Continued)

*Primary Examiner* — Kevin T Truong
*Assistant Examiner* — Tracy L Kamikawa
(74) *Attorney, Agent, or Firm* — Daniel J. Swirsky; ALPHAPATENT ASSOCIATES, LTD (57) ABSTRACT

A laryngoscope comprising a handle and a blade is provided. The blade is hingedly articulated to the handle between an open position wherein it projects outwardly from a top end of the handle, and a closed position wherein it lies in registration therewith. The laryngoscope further comprises an electric light source and a power source selectively electrically connected thereto for providing electric power for its operation. The blade comprises a power source compartment at the proximal end, containing therewithin the power source. The laryngoscope further comprises a switching arrangement configured to electrically connect between the electric light and power sources when the blade in its open position, and electrically separate between the electric light source and power source when the blade in its closed position. The handle comprises a depression for accommodating therein at least a portion of the blade when in its closed position.

14 Claims, 4 Drawing Sheets

(52) U.S. Cl.
CPC ............ *A61B 1/00066* (2013.01); *A61B 1/06* (2013.01); *A61B 1/0676* (2013.01)

(58) Field of Classification Search
CPC ... A61B 1/07; A61B 1/00025; A61B 1/00036; A61B 1/00066; A61B 1/00105; A61B 1/00149
See application file for complete search history.

(56) References Cited

U.S. PATENT DOCUMENTS

| | | | |
|---|---|---|---|
| 4,815,451 A * | 3/1989 | Bauman | A61B 1/267 600/198 |
| 4,924,862 A | 5/1990 | Levinson | |
| 5,060,633 A | 10/1991 | Gibson | |
| 5,438,976 A * | 8/1995 | Nash | A61B 1/267 600/186 |
| 5,664,560 A | 9/1997 | Merrick et al. | |
| 5,800,344 A | 9/1998 | Wood, Sr. et al. | |
| 6,213,937 B1 * | 4/2001 | Vivenzio | A61B 1/267 600/193 |
| 6,217,514 B1 | 4/2001 | Gruen et al. | |
| 6,634,356 B1 | 10/2003 | O'Dea et al. | |
| 6,719,688 B2 | 4/2004 | Pecherer et al. | |
| 6,964,637 B2 * | 11/2005 | Dalle | A61B 1/267 600/185 |
| 7,909,759 B2 * | 3/2011 | Pecherer | A61B 1/00032 600/193 |
| 8,162,826 B2 * | 4/2012 | Pecherer | A61B 1/00055 600/197 |
| 8,287,450 B1 * | 10/2012 | He | A61B 1/267 600/193 |
| 8,414,481 B2 | 4/2013 | Hakanen et al. | |
| 2007/0125374 A1 | 6/2007 | Smith et al. | |
| 2007/0167686 A1 * | 7/2007 | McGrath | A61B 1/00087 600/188 |
| 2008/0146878 A1 | 6/2008 | Frost et al. | |
| 2008/0242941 A1 | 10/2008 | Kim et al. | |
| 2009/0187078 A1 * | 7/2009 | Dunlop | A61B 1/267 600/179 |
| 2012/0330103 A1 | 12/2012 | Tenger et al. | |
| 2013/0060089 A1 * | 3/2013 | McGrath | A61B 1/267 600/187 |
| 2013/0104896 A1 | 5/2013 | Kimm et al. | |
| 2014/0171748 A1 * | 6/2014 | Bookwalter | A61B 17/02 600/231 |
| 2015/0282696 A1 * | 10/2015 | Sun | A61B 1/0684 600/214 |

FOREIGN PATENT DOCUMENTS

| | | | | |
|---|---|---|---|---|
| GB | 2491189 A | 11/2012 | | |
| WO | WO 2013083836 A1 * | 6/2013 | ............ | A61B 1/267 |
| WO | 2015036938 A1 | 3/2015 | | |

* cited by examiner

LARYNGOSCOPE

CROSS-REFERENCE TO RELATED APPLICATIONS

This application is a U.S. National Phase Application under 35 U.S.C. 371 of International Application No. PCT/IB2015/053747, which has an international filing date of May 21, 2015, and which claims priority and benefit from U.S. Provisional Pat. Application No. 62/001,649, filed May 22, 2014, the contents and disclosure of which are incorporated herein by reference in their entirety.

FIELD OF THE INVENTION

The present disclosure relates to laryngoscopes.

BACKGROUND OF THE INVENTION

Endotracheal tubes are utilized in a wide variety of medical procedures to provide an unobstructed air passage to a patient's trachea. In order to facilitate insertion of an endotracheal tube into a patient's airway, a laryngoscope may be used.

A laryngoscope typically comprises a blade, along which the endotracheal tube is guided, and a handle, which is manipulated to alter the position of the blade within the patient's airway. In addition, other features, such as lights, etc., may be provided.

SUMMARY OF THE INVENTION

According to one aspect of the presently disclosed subject matter, there is provided a laryngoscope comprising a handle and a blade hingedly articulated, at a proximal end thereof, to the handle between an open position wherein the blade projects outwardly from a top end of the handle, and a closed position wherein the blade lies in is registration with the handle, the laryngoscope further comprising an electric light source and a power source selectively electrically connected thereto for providing electric power for its operation, wherein:
- the blade comprises a power source compartment at the proximal end, containing therewithin the power source;
- the laryngoscope further comprises a switching arrangement configured to electrically connect between the electric light source and power source when the blade in its open position, and electrically separate between the electric light source and power source when the blade in its closed position; and
- the handle comprises a depression for accommodating therein at least a portion of the blade when in its closed position.

The power source compartment may further comprise a pair of contacts, each for contacting the power source and each being electrically connected between the power source and the electric light source when the blade is in the open position.

The blade may be configured such that at least one of the contacts is a movable contact not in contact with the power source when in the closed position, wherein the switching arrangement is configured to electrically connect between the electric light source and power source by biasing the movable contact toward the power source when the blade is in the open position.

The switching arrangement may comprise a linear cam and a follower configured to be biased thereby toward the power source when the blade is brought into its open position.

The handle may comprise an angled surface constituting the linear cam, with the blade comprising a flexible tab adjacent the movable contact and having a protrusion constituting the follower.

The power source may comprise a battery having two oppositely charged terminals. The battery may be a button cell.

The blade may be configured to pivot about a hinge axis with respect to the handle between its open and closed positions, wherein the power source compartment is configured to hold the battery such that the central axis is substantially parallel to the hinge axis.

The blade may comprise a removable cover providing access to the power source compartment when removed.

The depression may be configured to accommodate a distal end of the blade when in its closed position. A base of the depression may be at least partially defined by an angled surface, formed such that the distal end of the blade lies in registration therewith when in its closed position. A sidewall of the depression may be at least partially defined by a bottom portion of the handle. The depression may be formed such that it is defined only by the angled surface and the bottom portion.

The blade and handle may comprise a locking arrangement configured to retain the blade in its open position.

The locking arrangement may comprise a tab on the blade having an outwardly facing protrusion, and an aperture on the handle configured to receive therein the protrusion of the tab. The aperture may be through-going, thereby providing access to the tab when received therewithin.

The blade may comprise a flexible region located between the proximal and distal ends thereof, the flexible region comprising one or more features configured to increase the flexibility of the blade locally. The blade may comprise two substantially parallel surfaces extending in a direction along the length of the blade, and a vertical support wall extending therebetween and connected to each of the surfaces, wherein the feature comprises a gap, extending along the length, between the support wall and one of the surfaces.

The blade may comprise one or more open channels extending in a direction along its length. Each of the channels may define a path between the electric light source and the power source compartment. The laryngoscope may further comprise one or more conductive wires facilitating the electric connection between the electric light source and the power source and being received within the channels.

The blade may comprise:
- a first blade element comprising a lower horizontal surface and a vertical support wall; and
- a second blade element comprising an upper horizontal surface.

The first and second blade elements may be made of different materials.

The first blade element may be made of a metal, with the second blade element being made of a plastic material.

BRIEF DESCRIPTION OF THE DRAWINGS

For a better understanding of the examples and to show how it may be carried into effect, reference will now be made, purely by way of example, to the accompanying drawings.

With specific reference now to the drawings in detail, it is stressed that the particulars shown are by way of example and for purposes of illustrative discussion of selected examples only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the several selected examples may be put into practice. In the accompanying drawings:

FIGS. 1A and 1B are perspective view of a laryngoscope according to the presently disclosed subject matter, with a blade thereof in open and closed positions, respectively;

DETAILED DESCRIPTION

Figure 1A:
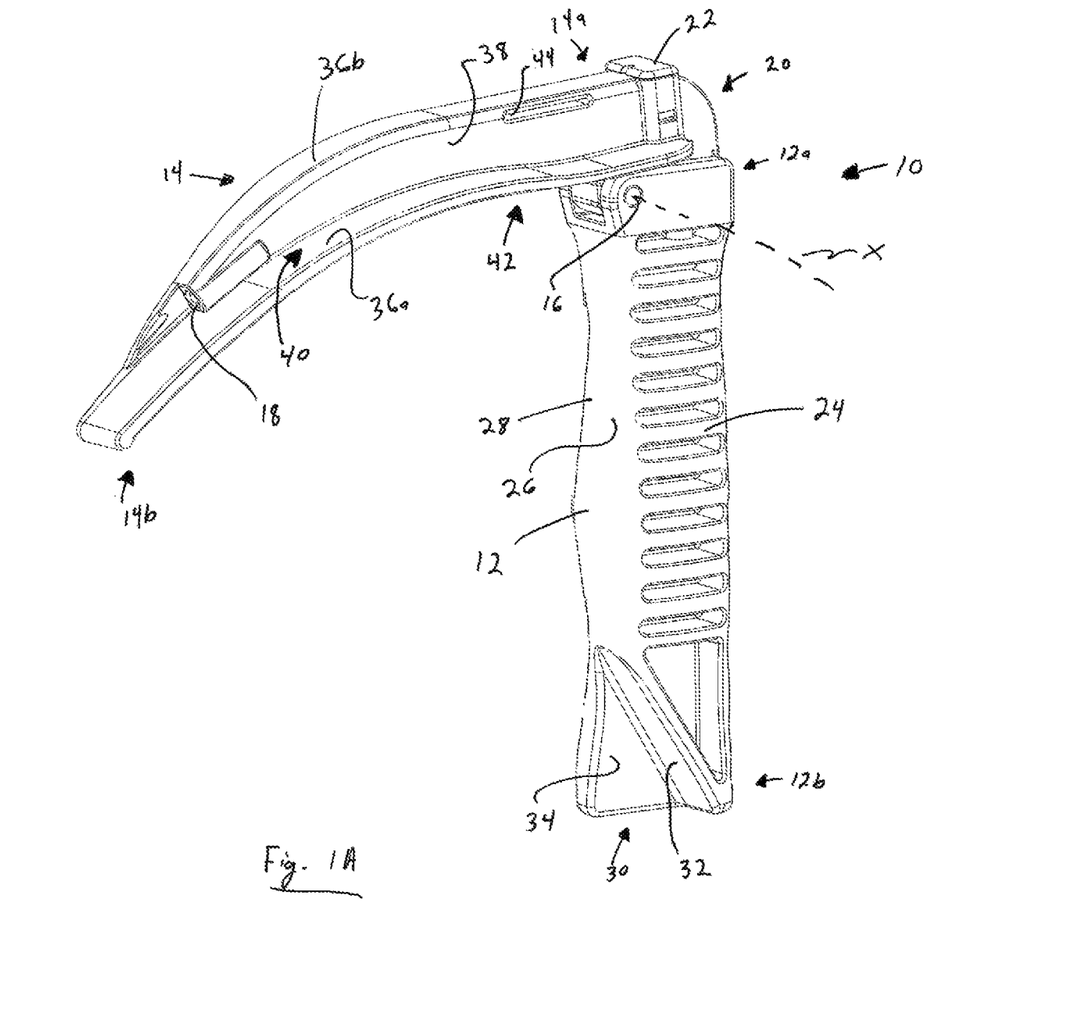

As illustrated in FIGS. 1A and 1B, there is provided a laryngoscope, which is generally indicated at 10. The laryngoscope 10 comprises a handle 12 and a blade 14 pivotally articulated thereto by a hinge 16. The hinge 16 facilitates attachment of a proximal end 14*a* of the blade 14 to a top end 12*a* of the handle 12. In addition, it facilitates articulation of the handle 14, about a hinge axis X, between an open position thereof (as in FIG. 1A), wherein the wherein the blade projects outwardly the top end 12*a* of the handle 12, and a closed position thereof (as in FIG. 1B), wherein the blade lies in registration with the handle.

The laryngoscope may be made of any suitable material or combination of materials. For example, the handle 12 and blade 14 may each be made of a plastic material, a metal material, or one may be made of a plastic material and the other of a metal material.

The laryngoscope 10 further comprises an electric light source 18 and a power source (not seen in FIGS. 1A and 1B) disposed within a power source compartment 20 formed in the proximal end 14*a* of the blade 14. The electric light source 18 may be any suitable element configured to provide illumination when connected to the power source, such as a light emitting diode. In addition to or instead of the light source, the laryngoscope may comprise a camera element (not illustrated) configured to provide a user with a view from the distal end 14*b* of the blade 14.

A removable cover 22 may be provided, configured to provide access to the power source compartment 20 when removed. As will be described below, the power source is selectively electrically connected to the electric light source 18 for providing electric power thereto, thereby facilitating its operation.

The laryngoscope 10 is further provided with a switching arrangement (not indicated in FIGS. 1A and 1B). The switching arrangement is configured to facilitate control of (i.e., the selectivity) of the electric connection between the electric light 18 source and the power source. It may be designed to connect between the electric light source 18 and the power source when the blade 14 in its open position, and electrically separate (i.e., break the connection) between the electric light source and the power source when the blade in its closed position.

The handle 12 comprises a grip 24, which may constitute most of its length, and may be designed to facilitate a user to hold the laryngoscope 10 comfortably. As such, it may be formed with rounded corners 26, and it may further comprise one or more rounded sides, e.g., a front side 28 thereof may be formed having a curved profile. Alternatively, it may be formed having any other suitable ergonomic design.

The handle 12 may be further designed to receive therein at least a portion of the blade 14 when in its closed position. This may facilitate a more compact arrangement of the laryngoscope 10 when not in use. Accordingly, a bottom end 12*b* of the handle 12 may be formed with a depression 30 for accommodating therein a distal end 14*b* of the blade 14 when in its closed position.

The depression 30 may be defined between a base 32 and a sidewall 34. As illustrated, the depression 30 has an open configuration, i.e., it is only defined between these two features of the handle 12 (e.g., there is no feature of the handle 12 opposite the sidewall 34 which defines the depression). Forming the depression 30 in such a way facilitates easy opening/closing of the blade 14. The base 32 may comprise an angled surface of the handle 12, formed such that the distal end 14b of the blade 14 lies in registration therewith (i.e., substantially on top of with little or no space therebetween, substantially parallel therewith, or aligned therewith) in its closed position.

As best seen in FIG. 1A, the blade 14 comprises upper and lower horizontal surfaces 36*a*, 36*b* (herein, reference numeral 36 will be used to refer to the horizontal surfaces collectively) substantially parallel to each other and extending along its length, and a vertical support wall 38 extending therebetween, connected to each of horizontal surfaces. The lower horizontal surface 36*b* and the support wall 38 may define a path 40, e.g., for guiding a tube into a patient's windpipe during intubation.

The blade 14 may be formed with a flexible region, which is generally indicated at 42, located in a central portion thereof, i.e., between its proximal end 14*a* and distal end 14*b*. The flexible region 42 is characterized as having an increased flexibility compared to the other portions of the blade 14. This imparts a tendency to the blade 14 to yield locally when a pressure is applied thereto.

Forming the blade 14 with the flexible region 42 may be useful, e.g., to moderate the effect of the blade 14 when inserted into a patient's mouth, as pressure which may be applied to the patient's teeth by the blade is mitigated by the flexibility. Thus, providing a blade 14 having a flexible region 42 may contribute to preventing or reducing dental injury in a patient during intubation. Accordingly, the blade 14 may be constructed such that the flexible region 42 is designed to be opposite a patient's teeth during intubation.

According to some example, the flexible region 42 comprises at least one longitudinal (i.e., extending in the direction of the length of the blade 14) gap 44 between the vertical support wall 38 and at least one of the horizontal surfaces 36. The gap provides different constituent elements of the blade 14 to shift with respect to one another, e.g., when different pressures are applied to them. The gap may be constituted by a through-going elongate aperture, as shown. Alternatively, it may be constituted by a blind (i.e., non-through-going) elongate aperture.

According to other examples, the flexible region 42 is provided by locally constructing the blade 14 or portion thereof to be of a lower thickness. (It will be appreciated that herein the specification and claims, the term "locally," in particular when used in the context of the flexible region, is used to describe the area under discussion, compared to the rest of the blade.)

According to examples wherein the blade 14 is made of a plastic or other suitable material, the selection of material may obviate the necessity to provide a physical feature to provide a flexible region. Accordingly, the entire blade 14 may, owing to properties of the material thereof, be sufficiently flexible to mitigate the risk of dental injury during intubation.

Figure 2:
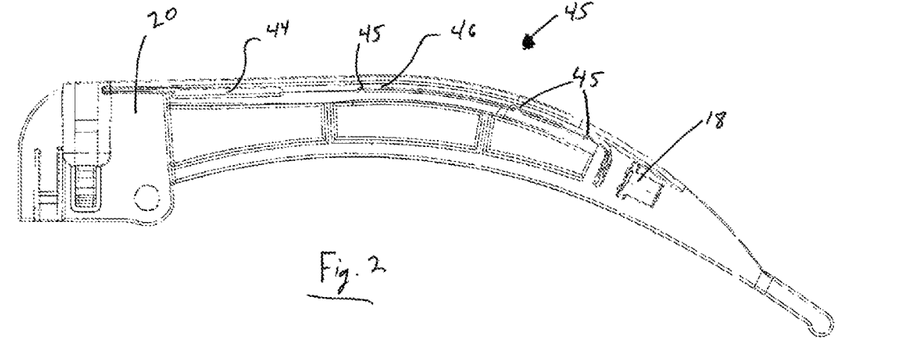
FIG. 2 is a left-side view of a blade of the laryngoscope illustrated in FIGS. 1A and 1B.

As illustrated in FIG. 2, the blade 14 may furthermore be provided with a longitudinal channel 46, extending between the electric light source 18 and the power source compartment 20, defining a path therebetween. One or more wires, (not illustrated) or any other suitable conductor, for facilitating an electrical connection between the electric light source 18 and the power source (disposed within the power source compartment 20) are received therein. The channel 46 may be open, thereby simplifying construction of the laryngoscope 10. One or more retention bumps 45 may be provided along its length to facilitate retention thereof of, e.g., the wire.

In addition to defining a path for wires electrically connecting between the electric light source 18 and the power source, the channel 46 imparts a degree of flexibility to the blade. The blade 14 may thus be provided with local flexibility, for example comprising a flexible region 42 as described above, flexibility along its entire (or most of its) length, or a combination of both, mutatis mutandis.

The blade 14 may be formed as one piece, or assembled from two pieces. The pieces may be made of the same material, or of different materials. According to some examples, one piece may comprise the lower horizontal surface 36b and the vertical support 38, with the second piece comprising the upper horizontal surface 36a. According to some modifications, the first piece comprises the lower horizontal surface 36b and an layer of the vertical support 38 facing it, while the second piece comprises the upper horizontal surface 36a, as well as portions of the blade 14 disposed therebelow. According to any of the above, the first piece may be made of metal, and the second of plastic. This construction may contribute to the overall flexibility of the blade 14.

Figure 3:
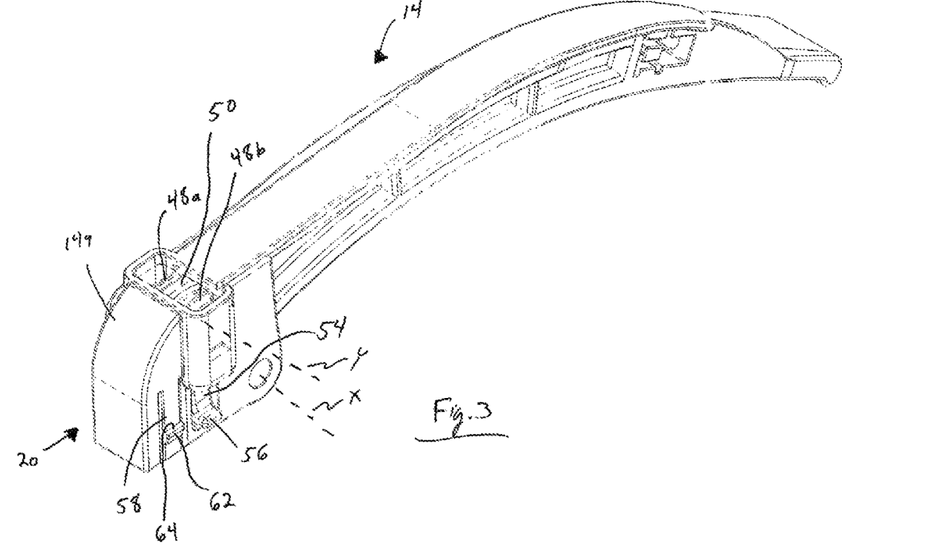
FIG. 3 is a rear left-side perspective view of the blade illustrated in FIG. 2.

As illustrated in FIG. 3, the power source compartment 20 comprises a pair of contacts 48a, 48b (herein, reference numeral 48 will be used to refer to the contacts collectively), held in place with relation to the power source 50, which may be a battery having two oppositely charged terminals. Wires (not illustrated) or any other suitable conductor, are provided to electrically connect the contacts 48 to the electric light source 18.

According to some examples, the power source 50 is a button cell, as illustrated. It is generally flat, with a throughgoing central axis Y. The power source compartment 20 is configured to maintain the power source 50 in a position such that the central axis Y thereof is substantially parallel to said hinge axis X. Accordingly, the power source 50 may be disposed with the blade 14, facilitating a compact construction of the laryngoscope 10.

Figure 4A:
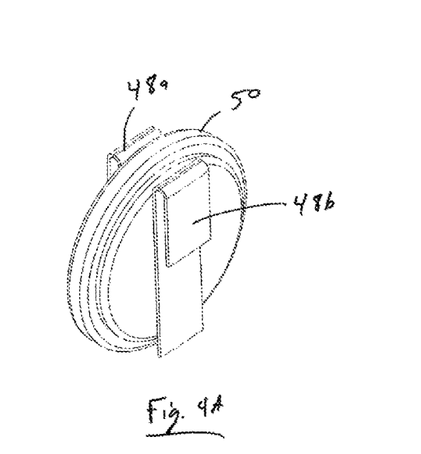
FIGS. 4A and 4B are rear left-side perspective and rear views, respectively, of power-related elements of the laryngoscope illustrated in FIGS. 1A and 1B.
Figure 4B:
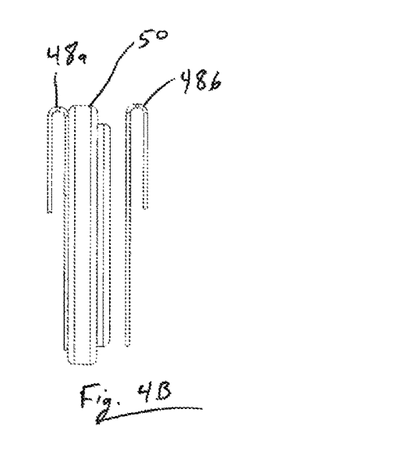

FIG. 4A illustrates the contacts 48 and power source 50 in the same positions and dispositions with respect to one another, and from the same perspective, as in FIG. 3, with the handle 14 removed from view. FIG. 4B illustrates the contacts 48 and power source 50 in the same positions and dispositions with respect to one another as in FIG. 3, but as seen from the back, in order to better show their positions, as will be described below.

As seen better in FIGS. 4A and 4B, the power source compartment 20 is constructed such that a permanent contact 48a is positioned to be in contact with the one terminal of the power source 48, irrespective of the position of the blade 14, and such that a moveable contact 48b is, in a rest state thereof, not in contact with the power source when not acted on by any external forces.

Figure 5:
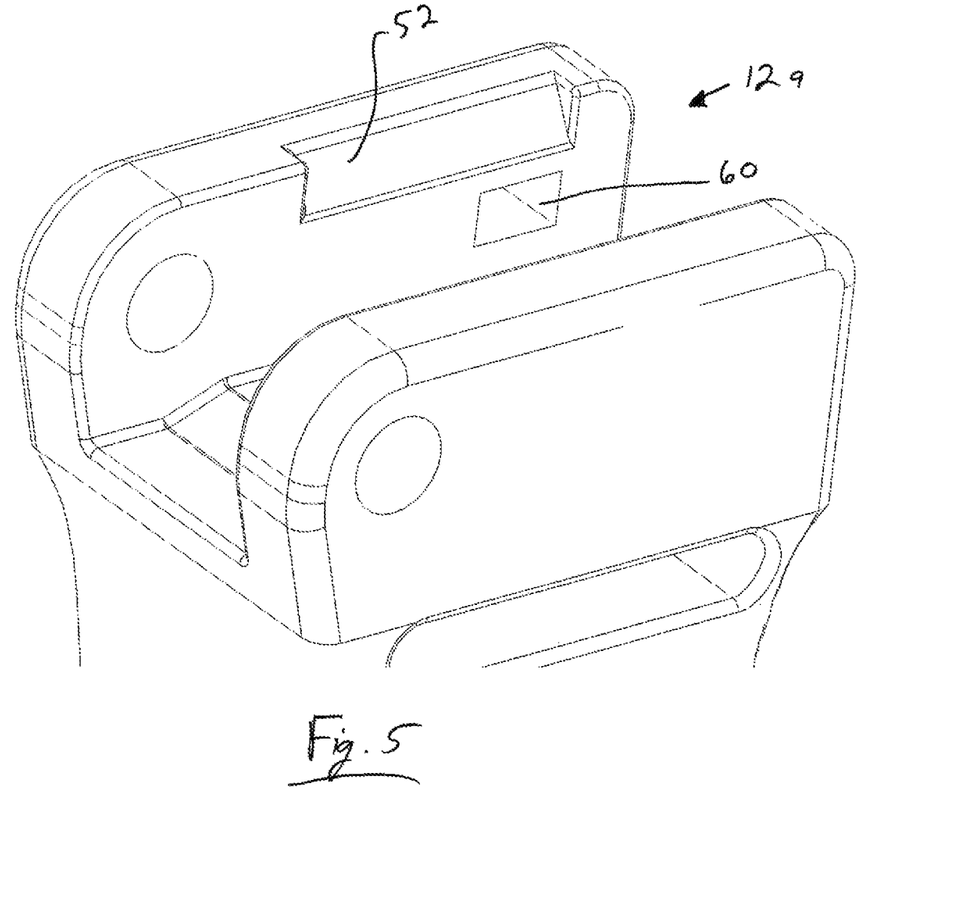
FIG. 5 is a front right-side perspective view of a top end of a handle of the laryngoscope illustrated in FIGS. 1A and 1B.

The switching arrangement is configured to bias the moveable contact 48b, when the blade 14 is in its open position, such that it comes into contact with the other terminal of the power source 50, thereby completing a circuit and facilitating turning on of the electric light source 18, as will be described below. Accordingly, as seen in FIG. 5, it may comprise an angled surface 52 formed on the top end 12a of the handle 12, and, reverting to FIG. 3, a flexible tab 54 formed on the proximal end 14a of the blade, adjacent to and exteriorly disposed from the moveable contact 48b. (It will be appreciated that as FIGS. 3 and 5 are seen from opposite sides of the laryngoscope, i.e., the handle 12 in FIG. 5 is configured to hold the blade 14 extending toward the left of the illustration, while in FIG. 3 the blade 14 extends toward the right side of the illustration. This has been done to properly illustrate all elements of the switching arrangement.) The flexible tab 54 may comprise an outwardly-facing protrusion 56 and is inwardly adjacent to the moveable contact 48b (e.g., the moveable contact may be positioned against an inwardly-facing side of the flexible tab).

The angled surface 52 constitutes a linear cam and the protrusion 56 constitutes a follower operating together to bias the moveable contact 48b toward the power source 50 as the blade 14 is moved into its open position. As the blade 14 is brought into its open position from the closed position, the protrusion 56 bears against the angled surface 52. The protrusion 56 is moved lower therealong by the opening of the blade 14, biasing it inwardly (i.e., toward the interior of the power source compartment 20 and the power source 50), and biasing with it the moveable contact 48b toward the power source 50, thereby completing the circuit, resulting in the electric light source 18 turning on.

The laryngoscope 10 may comprise a locking arrangement configured to retain the blade in its open position. The locking arrangement may comprise a locking tab 58 formed on the blade 14 and an inwardly-facing aperture 60 formed in the top end 12a of the handle 12. The locking tab 58 comprises an outwardly-facing locking protrusion 62, designed to be received within the aperture 60. The aperture 60 is disposed in a location corresponding to that of the locking protrusion 62 when the handle 14 is in its open position. In addition, it may be disposed below a portion of the angled surface 52, or below a separate but similar angled surface (not illustrated).

In use, when the blade 14 is brought into its open position, the locking protrusion 62 is received within the aperture 60. An upper surface 64 of the locking protrusion 62 bears against an inner surface of the aperture 60, preventing its release therefrom, and facilitating the blade 14 being locked in its open position. According to some examples, the aperture 60 is through-going, which provides access to a user to release the locking tab 58 when its locking protrusion 62 is received therewithin by applying an inwardly-directed force thereto. Thus, the blade 14 can be released from its open position and returned to its closed position at the discretion of the user.

According to examples wherein the aperture 60 is formed below the angled surface 52, the angled surface 52 constitutes a linear cam with the locking protrusion 62 constitutes a follower operating together, as described above with reference to the switching arrangement, mutatis mutandis.

Those skilled in the art to which this invention pertains will readily appreciate that numerous changes, variations and modifications can be made without departing from the scope of the invention mutatis mutandis.

Technical and scientific terms used herein should have the same meaning as commonly understood by one of ordinary skill in the art to which the disclosure pertains. Nevertheless, it is expected that during the life of a patent maturing from this application many relevant systems and methods will be developed.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the composition or method.

As used herein, the singular form "a", "an" and "the" may include plural references unless the context clearly dictates otherwise. For example, the term "a compound" or "at least one compound" may include a plurality of compounds, including mixtures thereof.

It is appreciated that certain features of the disclosure, which are, for clarity, described in the context of separate examples, may also be provided in combination in a single embodiment. Conversely, various features of the disclosure, which are, for brevity, described in the context of a single example, may also be provided separately or in any suitable subcombination or as suitable in any other described example of the disclosure. Certain features described in the context of various examples are not to be considered essential features of those examples, unless the example is inoperative without those elements.

Although the disclosure has been described in conjunction with specific examples thereof, it is evident that many alternatives, modifications and variations will be apparent to those skilled in the art. Accordingly, it is intended to embrace all such alternatives, modifications and variations that fall within the spirit and broad scope of the disclosure.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

The invention claimed is:

1. A laryngoscope comprising:
a handle;
a blade; and
a hinge configured to attach a proximal end of said blade to a top end of said handle such that said blade is hingedly articulated to said handle and adjustable between
an operative intubation position wherein said blade is generally perpendicular to said handle such that said blade projects outwardly from the top end of said handle, and
an inoperative storage position wherein said blade is co-directional with said handle such that said blade lies in registration with said handle,
said laryngoscope further comprising an electric light source and a power source selectively electrically connected thereto for providing electric power for its operation, wherein
the blade comprises a power source compartment at said proximal end, containing therewithin said power source, said power source compartment further comprising a pair of contacts, each for contacting the power source and each being electrically connected between the power source and said electric light source when the blade is in the operative intubation position, wherein at least one of said pair of contacts is a movable contact not in contact with the power source when in the inoperative storage position,
said laryngoscope further comprising a switching arrangement configured to electrically connect between said electric light source and said power source by biasing said movable contact toward said power source when the blade is in said operative intubation position, and electrically separate between said electric light source and said power source when the blade in said inoperative storage position, and
the handle comprises a depression for accommodating therein at least a portion of the blade when in said inoperative storage position, and
wherein said blade comprises a flexible region located between the proximal end and is distal ends thereof, said flexible region comprising one or more features configured to increase the flexibility of the blade locally, said blade comprising two substantially parallel horizontal surfaces extending in a direction along a length of the blade, and a vertical support wall extending therebetween and connected to each of said surfaces, wherein said feature comprises a gap, extending along said length, between said support wall and one of said horizontal surfaces, and
wherein said switching arrangement comprises a linear cam comprising an angled surface on said handle, and a follower comprising a protrusion on a flexible tab on said blade, wherein said flexible tab is adjacent said movable contact such that when said follower is biased inwardly by said linear cam when said blade is brought into its operative intubation position, said flexible tab biases said movable contact toward said power source to electrically connect between said electric light source and said power source.

2. The laryngoscope according to claim 1, wherein said blade comprises one or more channels extending in a direction along its length.

3. The laryngoscope according to claim 2, wherein each of said one or more channels extends between and defines a path between said electric light source and said power source compartment.

4. The laryngoscope according to claim 3, further comprising one or more conductive wires facilitating the electric connection between the electric light source and the power source and being received within said channels.

5. The laryngoscope according to claim 1, said blade being configured to pivot about a hinge axis with respect to said handle between its operative intubation and inoperative storage positions, wherein said power source compartment is configured to hold said power source such that a central axis of said power source is substantially parallel to said hinge axis.

6. The laryngoscope according to claim 1, wherein said blade comprises a removable cover providing access to said power source compartment when removed.

7. The laryngoscope according to claim 1, wherein said depression is configured to accommodate the distal end of said blade when in its inoperative storage position.

8. The laryngoscope according to claim 7, wherein a base of said depression is at least partially defined by an angled surface, formed such that the distal end of said blade lies in registration therewith when in its inoperative storage position.

9. The laryngoscope according to claim 7, wherein a sidewall of said depression is at least partially defined by a bottom portion of said handle.

10. The laryngoscope according to claim 1, wherein said blade and said handle comprise a locking arrangement configured to retain the blade in its operative intubation position.

11. The laryngoscope according to claim 10, wherein said locking arrangement comprises a tab on said blade having an outwardly facing protrusion, and an aperture on said handle configured to receive therein the protrusion of said tab.

12. The laryngoscope according to claim 11, wherein said aperture is through-going, thereby providing access to the tab when received therewithin.

13. The laryngoscope according to claim 1, wherein said blade comprises:
    a first blade element comprising a lower horizontal surface of the two substantially parallel horizontal surfaces and the vertical support wall; and
    a second blade element comprising an upper horizontal surface of the two substantially parallel horizontal surfaces.

14. The laryngoscope according to 13, wherein said first blade element is made of a metal, and said second blade element is made of a plastic material.

* * * * *